(12) United States Patent
Smith et al.

(10) Patent No.: US 9,216,304 B2
(45) Date of Patent: *Dec. 22, 2015

(54) METHOD OF DEPILATION AND DEPILATORY KIT

(75) Inventors: Charles Robert Smith, Henley on Thames (GB); Stuart Andrew Hewlins, Woking (GB); Michael John Goffe, Egham (GB)

(73) Assignee: The Gillette Company, Boston, MA (US)

( * ) Notice: Subject to any disclaimer, the term of this patent is extended or adjusted under 35 U.S.C. 154(b) by 190 days.

This patent is subject to a terminal disclaimer.

(21) Appl. No.: 13/070,775

(22) Filed: Mar. 24, 2011

(65) Prior Publication Data

US 2011/0238086 A1    Sep. 29, 2011

(30) Foreign Application Priority Data

Mar. 26, 2010  (EP) .................... 10158066

(51) Int. Cl.
*A61Q 9/04*         (2006.01)
*A61K 8/46*         (2006.01)
*A61K 8/37*         (2006.01)

(52) U.S. Cl.
CPC . *A61Q 9/04* (2013.01); *A61K 8/375* (2013.01); *A61K 8/46* (2013.01); *A61K 2800/88* (2013.01); *A61K 2800/884* (2013.01)

(58) Field of Classification Search
USPC .......................................................... 424/73
See application file for complete search history.

(56) References Cited

U.S. PATENT DOCUMENTS

| | | |
|---|---|---|
| 2,202,829 A | 6/1940 | Buff |
| 2,425,696 A | 8/1947 | Herrmann |
| 2,954,324 A | 9/1960 | Brummer |
| 3,194,736 A | 7/1965 | Braun et al. |
| 3,384,548 A | 5/1968 | Zviak et al. |
| 3,527,559 A | 9/1970 | Sliwinski |
| 3,563,694 A | 2/1971 | Minton |
| 3,567,363 A | 3/1971 | Wolfram |
| 3,728,356 A | 4/1973 | Yablonsky |
| 3,754,035 A | 8/1973 | Grayson |
| 3,766,275 A | 10/1973 | Ciaudelli |
| 3,808,637 A | 5/1974 | Lapidus |
| 3,827,938 A | 8/1974 | Aunstrup et al. |
| 3,843,780 A | 10/1974 | Michaels et al. |
| 3,865,546 A | 2/1975 | Zemlin et al. |
| 3,981,681 A | 9/1976 | De La Guardia |
| 4,088,751 A | 5/1978 | Kenkare et al. |
| 4,111,653 A | 9/1978 | Lindemann et al. |
| 4,121,904 A | 10/1978 | Schamper |
| 4,152,784 A | 5/1979 | McGalliard |
| 4,161,612 A | 7/1979 | Suzuki |
| 4,177,260 A | 12/1979 | Wajaroff |
| 4,282,877 A | 8/1981 | Mathews |
| 4,370,315 A | 1/1983 | Greff et al. |
| 4,401,663 A | 8/1983 | Buckwalter et al. |
| 4,424,205 A | 1/1984 | LaHann et al. |
| 4,443,473 A | 4/1984 | Buckwalter et al. |
| 4,460,602 A | 7/1984 | Buckwalter et al. |
| 4,498,474 A | 2/1985 | Chalmers |
| 4,546,112 A | 10/1985 | LaHann et al. |
| 4,618,344 A | 10/1986 | Wells |
| 4,734,099 A | 3/1988 | Cyprien |

(Continued)

FOREIGN PATENT DOCUMENTS

| | | |
|---|---|---|
| AU | 8315818 A4 | 8/1982 |
| AU | 9229690 A4 | 5/1993 |

(Continued)

OTHER PUBLICATIONS

Samion et al, Ability of Moisturizers to Reduce Dry Skin and Irritation and to Prevent their Return, J. Cosmet. Sci., 56, 427-444 (2005).*

(Continued)

*Primary Examiner* — Jennifer A Berrios
(74) *Attorney, Agent, or Firm* — Ronald Terk Sia; Kevin C. Johnson; Steven W. Miller

(57) ABSTRACT

A method of removing hair from skin, preferably facial skin, is provided, comprising the steps of:

(a) applying a hydrophobic protective composition to an area of skin, preferably facial skin, on which unwanted hair is growing, the hydrophobic protective composition comprising 20% or more, preferably 50% or more and more preferably from 75% to 99% of at least one triglyceride by weight of the hydrophobic protective composition, the or each triglyceride having the following formula:

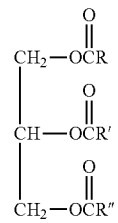

wherein R, R' and R" may be the same as or different from one or both of the others, wherein each of R, R' and R" is a fatty acid and wherein the or each triglyceride is solid at 25° C.

(b) applying a depilatory composition to the area of skin to which the hydrophobic protective composition has been applied, the depilatory composition comprising a keratin reducing agent.

10 Claims, 1 Drawing Sheet

(56) References Cited

U.S. PATENT DOCUMENTS

| | | | |
|---|---|---|---|
| 4,738,841 A | 4/1988 | Pigiet | |
| 4,830,633 A | 5/1989 | Hori et al. | |
| 4,832,949 A | 5/1989 | Royal | |
| 4,842,610 A | 6/1989 | Gordon et al. | |
| 4,894,223 A | 1/1990 | Pigiet | |
| 4,923,478 A | 5/1990 | Naggiar | |
| 4,981,682 A | 1/1991 | Boothroyd et al. | |
| 5,023,371 A | 6/1991 | Tsui et al. | |
| 5,026,542 A * | 6/1991 | Baines et al. | 424/73 |
| 5,154,919 A | 10/1992 | Des Garets | |
| 5,158,765 A | 10/1992 | Qasem | |
| 5,220,064 A | 6/1993 | Johnson | |
| 5,271,942 A | 12/1993 | Heverhagen | |
| 5,319,136 A | 6/1994 | Sandler | |
| 5,378,455 A | 1/1995 | Kealey et al. | |
| 5,417,966 A | 5/1995 | Futami | |
| 5,419,895 A | 5/1995 | Kubo et al. | |
| 5,494,657 A | 2/1996 | Swenson | |
| 5,554,608 A | 9/1996 | Ahluwalia et al. | |
| 5,618,522 A | 4/1997 | Kaleta | |
| 5,645,825 A | 7/1997 | Hillebrand | |
| 5,648,394 A | 7/1997 | Boxall | |
| 5,669,916 A | 9/1997 | Anderson | |
| 5,698,187 A | 12/1997 | Naggiar | |
| 5,725,847 A | 3/1998 | De La Mettrie et al. | |
| 5,756,077 A | 5/1998 | Syed et al. | |
| 5,840,765 A | 11/1998 | Miller | |
| 5,843,420 A | 12/1998 | Bauer et al. | |
| 5,846,252 A | 12/1998 | Mehl, Sr. | |
| 5,897,857 A | 4/1999 | Hillebrand et al. | |
| 6,019,962 A | 2/2000 | Rabe et al. | |
| 6,020,006 A | 2/2000 | Styczynski et al. | |
| 6,027,513 A | 2/2000 | Massana Florensa | |
| 6,071,503 A | 6/2000 | Drechsler et al. | |
| 6,074,654 A | 6/2000 | Drechsler et al. | |
| 6,075,052 A | 6/2000 | Suzuki et al. | |
| 6,139,823 A | 10/2000 | Drechsler et al. | |
| 6,203,784 B1 | 3/2001 | Martin et al. | |
| 6,231,846 B1 | 5/2001 | Perring et al. | |
| 6,235,737 B1 | 5/2001 | Styczynski et al. | |
| 6,299,865 B1 | 10/2001 | Styczynski et al. | |
| 6,306,380 B1 | 10/2001 | Desmots et al. | |
| 6,336,462 B1 | 1/2002 | Santelli et al. | |
| 6,340,466 B1 | 1/2002 | Drechsler | |
| 6,375,948 B1 | 4/2002 | Tsuji et al. | |
| 6,406,683 B1 | 6/2002 | Drechsler | |
| 6,425,891 B1 | 7/2002 | Tapper | |
| 6,479,043 B1 | 11/2002 | Tietjen et al. | |
| 6,489,291 B1 | 12/2002 | Suzuki et al. | |
| 6,533,775 B1 | 3/2003 | Rizoiu | |
| 6,555,097 B1 | 4/2003 | Rabe | |
| 6,884,772 B1 | 4/2005 | Ohuchi et al. | |
| 7,871,633 B2 | 1/2011 | Bekele | |
| D670,568 S | 11/2012 | Pietila | |
| 2002/0146380 A1 | 10/2002 | Nambu | |
| 2002/0187181 A1 | 12/2002 | Godbey | |
| 2003/0118535 A1 | 6/2003 | Lustbader | |
| 2003/0175333 A1 | 9/2003 | Shefer | |
| 2003/0180242 A1 | 9/2003 | Eccard | |
| 2003/0183658 A1 | 10/2003 | Sartin | |
| 2003/0186826 A1 | 10/2003 | Eccard | |
| 2004/0077593 A1 | 4/2004 | Marron | |
| 2004/0096164 A1 | 5/2004 | Guttmann | |
| 2004/0180014 A1 | 9/2004 | Gupta | |
| 2004/0219118 A1 * | 11/2004 | Slavtcheff et al. | 424/70.1 |
| 2005/0124984 A1 | 6/2005 | Wagnieres | |
| 2006/0002878 A1 | 1/2006 | Acher et al. | |
| 2006/0034874 A1 | 2/2006 | Winston | |
| 2006/0204469 A1 * | 9/2006 | Spengler et al. | 424/70.31 |
| 2007/0098667 A1 | 5/2007 | Taneri | |
| 2007/0154442 A1 | 7/2007 | Hattendorf | |
| 2007/0292459 A1 | 12/2007 | Cooper | |
| 2008/0138304 A1 | 6/2008 | Biggs | |
| 2008/0200861 A1 | 8/2008 | Shalev | |
| 2008/0260671 A1 | 10/2008 | De La Torre | |
| 2009/0005462 A1 | 1/2009 | Gunn | |
| 2009/0068119 A1 | 3/2009 | Cawthorne | |
| 2009/0093749 A1 | 4/2009 | Shalev | |
| 2009/0117068 A1 | 5/2009 | Ellis | |
| 2009/0158595 A1 | 6/2009 | Acher | |
| 2009/0291148 A1 | 11/2009 | Breyfogle | |
| 2010/0083443 A1 | 4/2010 | Tindal | |
| 2012/0016381 A1 | 1/2012 | Hassan | |
| 2012/0272985 A1 | 11/2012 | Smith | |
| 2012/0272986 A1 | 11/2012 | Smith | |
| 2012/0272987 A1 | 11/2012 | Smith | |
| 2012/0272988 A1 | 11/2012 | Smith | |
| 2012/0272989 A1 | 11/2012 | Smith | |
| 2012/0276176 A1 | 11/2012 | Smith | |
| 2013/0042417 A1 | 2/2013 | Dring | |
| 2013/0042418 A1 | 2/2013 | Broyles | |
| 2013/0042419 A1 | 2/2013 | Broyles | |
| 2013/0047347 A1 | 2/2013 | Smith | |
| 2013/0047348 A1 | 2/2013 | Smith | |

FOREIGN PATENT DOCUMENTS

| | | |
|---|---|---|
| AU | 706320 B2 | 6/1999 |
| AU | 2008100175 A4 | 4/2008 |
| BE | 626897 | 1/1963 |
| BE | 1006810 A6 | 12/1994 |
| BE | 1007487 A3 | 7/1995 |
| BR | 8505576 A | 6/1987 |
| BR | 8706739 A | 11/1988 |
| BR | 9504105 A | 9/1997 |
| BR | 9601468 A | 3/1998 |
| BR | 9804114 A | 5/2000 |
| BR | 200000401 A4 | 8/2001 |
| BR | 200000324 A4 | 9/2001 |
| BR | 200004387 A4 | 11/2004 |
| BR | 200501467 A4 | 11/2006 |
| BR | 200503247 A4 | 12/2006 |
| BR | 200603838 A4 | 2/2007 |
| BR | 200600753 A4 | 11/2007 |
| BR | 200603466 A4 | 2/2008 |
| CA | 895839 A | 3/1972 |
| CA | 908055 A | 8/1972 |
| CA | 604711 A5 | 9/1978 |
| CA | 1161366 A1 | 1/1984 |
| CA | 1166577 A1 | 5/1984 |
| CA | 2149347 A1 | 12/1996 |
| CA | 2289879 A1 | 5/2001 |
| CA | 2354929 A1 | 2/2002 |
| CA | 2354829 | 2/2003 |
| CA | 2354829 A1 | 2/2003 |
| CA | 2555095 A1 | 2/2008 |
| CH | 525674 A | 7/1972 |
| CH | 670044 A5 | 5/1989 |
| CN | 1365659 A | 8/2002 |
| CN | 1398578 A | 2/2003 |
| CN | 100358491 C | 7/2006 |
| CN | 1868446 A | 11/2006 |
| CN | 1994259 A | 7/2007 |
| DE | 2131630 A1 | 1/1972 |
| DE | 2115423 A1 | 10/1972 |
| DE | 2166691 A1 | 6/1975 |
| DE | 3338957 A1 | 5/1985 |
| DE | 3339104 A1 | 5/1985 |
| DE | 3541485 A1 | 5/1987 |
| DE | 3828709 A1 | 3/1990 |
| DE | 4206692 A1 | 9/1993 |
| DE | 4325079 A1 | 1/1995 |
| DE | 209964 | 7/1995 |
| DE | 209964 A1 | 7/1995 |
| DE | 19735305 A1 | 2/1999 |
| DE | 19826529 A1 | 12/1999 |
| DE | 20204421 U1 | 6/2002 |
| DE | 20207366 U1 | 9/2002 |
| DE | 10208148 A1 | 2/2004 |
| DE | 10344963 A1 | 4/2005 |
| DE | 60022892 T2 | 7/2006 |
| DE | 102005042236 A1 | 3/2007 |
| DE | 102006020976 A1 | 11/2007 |
| EP | 18668 A1 | 11/1980 |

(56) References Cited

FOREIGN PATENT DOCUMENTS

| | | |
|---|---|---|
| EP | 95916 | 12/1983 |
| EP | 0085894 | 3/1984 |
| EP | 0095916 | 8/1984 |
| EP | 0089710 | 7/1985 |
| EP | 150948 A1 | 7/1985 |
| EP | 194181 A1 | 9/1986 |
| EP | 0161681 | 4/1987 |
| EP | 236219 A1 | 9/1987 |
| EP | 165970 A1 | 12/1987 |
| EP | 287773 A1 | 11/1988 |
| EP | 302265 A1 | 2/1989 |
| EP | 368698 A1 | 5/1990 |
| EP | 354554 C | 7/1991 |
| EP | 648488 A1 | 4/1995 |
| EP | 649646 A1 | 4/1995 |
| EP | 795314 A1 | 9/1997 |
| EP | 800815 A1 | 7/1999 |
| EP | 1001735 A1 | 5/2000 |
| EP | 1053046 A2 | 11/2000 |
| EP | 855900 C | 3/2001 |
| EP | 958808 A3 | 5/2001 |
| EP | 1094783 A1 | 5/2001 |
| EP | 1148865 A1 | 10/2001 |
| EP | 1245220 A1 | 10/2002 |
| EP | 1312353 | 5/2003 |
| EP | 10156297 A1 | 5/2003 |
| EP | 1368493 A2 | 12/2003 |
| EP | 1402679 A2 | 3/2004 |
| EP | 1482819 A1 | 12/2004 |
| EP | 1551250 A1 | 7/2005 |
| EP | 1582200 A1 | 10/2005 |
| EP | 1588690 A1 | 10/2005 |
| EP | 1604690 A1 | 12/2005 |
| EP | 2050433 A1 | 4/2006 |
| EP | 1726292 A1 | 11/2006 |
| EP | 1726297 A1 | 11/2006 |
| EP | 1779898 A1 | 5/2007 |
| EP | 1782860 A1 | 5/2007 |
| EP | 1844786 A1 | 10/2007 |
| EP | 1859785 A1 | 11/2007 |
| EP | 1902752 | 3/2008 |
| EP | 1967178 A1 | 9/2008 |
| EP | 2286768 A2 | 2/2011 |
| EP | 2356918 A1 | 8/2011 |
| EP | 2356962 A1 | 8/2011 |
| EP | 2356963 A1 | 8/2011 |
| EP | 2356964 A1 | 8/2011 |
| EP | 2356965 A1 | 8/2011 |
| EP | 2356966 A1 | 8/2011 |
| EP | 2356967 A1 | 8/2011 |
| EP | 2356968 A1 | 8/2011 |
| EP | 2368542 | 9/2011 |
| EP | 2368541 | 10/2011 |
| ES | 2005490 A6 | 3/1989 |
| ES | 2080701 A1 | 2/1996 |
| ES | 2119718 A1 | 10/1998 |
| ES | 2180439 A1 | 2/2003 |
| FR | 2020804 A1 | 7/1970 |
| FR | 2038196 A1 | 1/1971 |
| FR | 2087987 A1 | 1/1972 |
| FR | 2105039 A1 | 4/1972 |
| FR | 2168202 A1 | 8/1973 |
| FR | 2170113 A1 | 9/1973 |
| FR | 2204398 A1 | 5/1974 |
| FR | 2267755 A1 | 11/1975 |
| FR | 2347040 | 11/1977 |
| FR | 2377193 A1 | 8/1978 |
| FR | 2485927 A1 | 1/1982 |
| FR | 2541894 A1 | 9/1984 |
| FR | 2546405 A1 | 11/1984 |
| FR | 2547724 A3 | 12/1984 |
| FR | 2571615 A1 | 4/1986 |
| FR | 2572280 A1 | 5/1986 |
| FR | 2585566 A1 | 2/1987 |
| FR | 2626468 A1 | 8/1989 |
| FR | 2631825 A1 | 12/1989 |
| FR | 2637498 A1 | 4/1990 |
| FR | 2642647 A1 | 8/1990 |
| FR | 2656524 A1 | 7/1991 |
| FR | 2722405 A1 | 1/1996 |
| FR | 2749509 A1 | 12/1997 |
| FR | 2751873 A1 | 2/1998 |
| FR | 2752379 A1 | 2/1998 |
| FR | 2761262 A1 | 10/1998 |
| FR | 2764490 A1 | 12/1998 |
| FR | 2791255 A1 | 9/2000 |
| FR | 2794622 A1 | 12/2000 |
| FR | 2798064 A1 | 3/2001 |
| FR | 2883169 A1 | 9/2006 |
| FR | 2902998 A1 | 1/2008 |
| FR | 2924928 A1 | 6/2009 |
| GB | 1064388 A | 4/1967 |
| GB | 1192603 A | 5/1970 |
| GB | 1242083 A | 8/1971 |
| GB | 1260227 A | 1/1972 |
| GB | 1264319 | 2/1972 |
| GB | 1264319 | 2/1972 |
| GB | 1291377 A | 10/1972 |
| GB | 1296356 A | 11/1972 |
| GB | 1329029 A | 9/1973 |
| GB | 1348760 A | 3/1974 |
| GB | 1381669 A | 1/1975 |
| GB | 1484792 A | 9/1977 |
| GB | 1488448 A | 10/1977 |
| GB | 2113994 A | 8/1983 |
| GB | 2157951 A | 11/1985 |
| GB | 2231494 A | 11/1990 |
| GB | 2232587 A | 12/1990 |
| GB | 2287690 A | 9/1995 |
| GB | 2295771 A | 6/1996 |
| GB | 2306323 | 1/1998 |
| GB | 2326335 A | 12/1998 |
| GB | 2327190 A | 1/1999 |
| GB | 2336535 A | 10/1999 |
| GB | 2336536 A | 10/1999 |
| GB | 2337460 A | 11/1999 |
| GB | 2367749 A | 4/2002 |
| GB | 2391475 A | 2/2004 |
| GB | 2413074 A | 10/2005 |
| GB | 2429055 A | 2/2007 |
| GB | 2429914 A | 3/2007 |
| GB | 2447026 A | 9/2008 |
| HU | 200204564 | 11/2004 |
| HU | 200402393 A | 1/2007 |
| IT | 1273006 B | 7/1997 |
| IT | 1307085 B1 | 10/2000 |
| JP | 71037600 A | 10/1968 |
| JP | 74046065 A | 9/1970 |
| JP | 77002980 A | 4/1975 |
| JP | 60202810 A | 10/1985 |
| JP | 61212513 A | 9/1986 |
| JP | 61221112 A | 10/1986 |
| JP | 61254514 A | 11/1986 |
| JP | 61282311 A | 12/1986 |
| JP | 62230711 A | 10/1987 |
| JP | 63073910 A | 4/1988 |
| JP | 63203608 A | 8/1988 |
| JP | 63313718 A | 12/1988 |
| JP | 2300112 A | 12/1990 |
| JP | 5170624 A | 7/1993 |
| JP | 5180827 A | 7/1993 |
| JP | 5294816 A | 11/1993 |
| JP | 6135825 A | 5/1994 |
| JP | 6135826 A | 5/1994 |
| JP | 6157257 A | 6/1994 |
| JP | 06192056 | 7/1994 |
| JP | 6192056 A | 7/1994 |
| JP | 6192057 A | 7/1994 |
| JP | 6192058 A | 7/1994 |
| JP | 6225810 A | 8/1994 |
| JP | 6225811 A | 8/1994 |
| JP | 6235825 A | 8/1994 |
| JP | 6345662 A | 12/1994 |
| JP | 95064712 A | 7/1995 |

(56) References Cited

FOREIGN PATENT DOCUMENTS

| | | |
|---|---|---|
| JP | 8133936 A | 5/1996 |
| JP | 8283131 A | 10/1996 |
| JP | 9103320 A | 4/1997 |
| JP | 10139639 A | 5/1998 |
| JP | 10218731 C | 8/1998 |
| JP | 11012123 A | 1/1999 |
| JP | 11060451 A | 3/1999 |
| JP | 11106321 A | 4/1999 |
| JP | 2002204716 A | 7/2002 |
| JP | 2003040751 A | 2/2003 |
| JP | 2004244402 A | 9/2004 |
| JP | 2005170850 A | 6/2005 |
| JP | 2005170930 A | 6/2005 |
| JP | 2005187361 A | 7/2005 |
| JP | 2005187443 A | 7/2005 |
| JP | 2005200352 A | 7/2005 |
| JP | 2005200353 A | 7/2005 |
| JP | 2005224389 A | 8/2005 |
| JP | 2005232163 A | 9/2005 |
| JP | 2005330227 A | 12/2005 |
| JP | 2005330228 A | 12/2005 |
| JP | 2006008657 A | 1/2006 |
| JP | 2006016373 A | 1/2006 |
| JP | 2006028045 A | 2/2006 |
| JP | 2006045148 A | 2/2006 |
| JP | 2006096750 A | 4/2006 |
| JP | 2006182660 A | 7/2006 |
| JP | 2006298808 A | 11/2006 |
| JP | 2007145738 A | 6/2007 |
| JP | 2007217369 A | 8/2007 |
| JP | 2008007526 A | 1/2008 |
| KR | 97009776 A | 6/1997 |
| KR | 99065207 A | 1/1998 |
| KR | 99068483 A | 5/1999 |
| KR | 2000009533 A | 2/2000 |
| KR | 2000030722 A | 6/2000 |
| KR | 2000031349 A | 6/2000 |
| KR | 2000032466 A | 6/2000 |
| KR | 2000036534 A | 7/2000 |
| KR | 2000053859 A | 9/2000 |
| KR | 2005072302 A | 7/2005 |
| KR | 2005072303 A | 7/2005 |
| WO | 8906122 A | 7/1989 |
| WO | 9110421 | 7/1991 |
| WO | WO9110421 | 7/1991 |
| WO | 9308791 | 5/1993 |
| WO | 9308791 A1 | 5/1993 |
| WO | WO9308791 | 5/1993 |
| WO | 9421216 | 9/1994 |
| WO | WO9421216 | 9/1994 |
| WO | 9621419 A1 | 7/1996 |
| WO | 9825581 A1 | 6/1998 |
| WO | 9902125 | 1/1999 |
| WO | WO9902125 | 1/1999 |
| WO | 9936031 A1 | 7/1999 |
| WO | 0243682 A1 | 6/2002 |
| WO | 02092049 A | 12/2002 |
| WO | 03075812 | 9/2003 |
| WO | 2004096164 A1 | 11/2004 |
| WO | WO2004096164 | 11/2004 |
| WO | 2007046097 A2 | 4/2007 |
| WO | 2007119227 | 10/2007 |
| WO | 2007031793 | 6/2008 |
| WO | WO2007031793 | 6/2008 |
| WO | 2009002049 | 12/2008 |
| WO | 2008110745 | 1/2009 |
| WO | WO2008110745 | 1/2009 |
| WO | 2009042026 | 4/2009 |
| WO | WO2009042026 | 4/2009 |
| WO | 2009083836 | 7/2009 |
| WO | 2009090362 | 7/2009 |
| WO | 2010064017 A2 | 6/2010 |
| WO | 2011103220 A1 | 8/2011 |
| WO | 2011103221 A1 | 8/2011 |
| WO | 2011103222 A1 | 8/2011 |
| WO | 2011103227 A1 | 8/2011 |
| WO | 2011103229 A1 | 8/2011 |
| WO | 2011103230 A2 | 8/2011 |
| WO | 2011103231 A1 | 8/2011 |
| WO | 2011103232 A1 | 8/2011 |
| WO | 2011103233 A1 | 8/2011 |
| WO | 2011103234 A1 | 8/2011 |
| WO | 2011103250 A1 | 8/2011 |
| WO | 2011103251 A1 | 8/2011 |
| WO | 2011103252 A1 | 8/2011 |
| WO | 2011103253 A1 | 8/2011 |
| WO | 2011119328 A1 | 9/2011 |
| WO | 2011119557 A2 | 9/2011 |
| WO | 2011119794 A2 | 9/2011 |

OTHER PUBLICATIONS

Zhang et al, Near infrared imaging for measuring and visualizing skin hydration. A comparison with visual assessment and electrical methods, Journal of Biomedical Optics 10(3), May/Jun. 2005, p. 1-7.*
Chemical Abstracts, vol. 81, No. 17, Oct. 28, 1974, "Synthesis of Homovanillic Acid Derivatives of Capsaicin-Like Effect", P. Hegyes, et al., 7 pages.
International Search Report, Application No. PCT/US2011/028580, Mar. 16, 2011; 98 pgs.
European Search Report; App. No. 11165158,4-2108—Mailing Date Aug. 11, 2011; 6 pages.
International Search Report; PCT/US2012/0233988; Mailing Date May 31, 2012; 11 pages.
European Search Report; App. No. 11165166.7-2108; Mailing Date Sep. 13, 2011; 6 pages.
European Search Report 11181559.3-2108; Mailing Date Jan. 2, 2012; 7 pages.
Sensitive Hair Removal & Finishing Creme Set, Record ID 1327122; Boots Co.; 4 pages, 2010.
P. Hegyes; Chemical Abstracts, vol. 81, No. 17, Oct. 28, 1974, "Synthesis of Homovanillic Acid Derivatives of Capsaicin-Like Effect", P. Hegyes, et al., 7 pagesChemical Abstracts, vol. 81, No. 17, Oct. 28, 1974, "Synthesis of Homovanillic Acid Derivatives of Capsaicin-Like Effect"., 7 pages.
Arzneimittel-Forschung, vol. 25, No. 12, Dec. 1975, "Sensory Effects of Capsaicin Congeners—Relationship Between Chemical Structure and Pain-Producing Potency of Pungent Agents", 5 pages.
International Search Report, Application No. PCT/US2011/028580, Mar. 16, 2011; 12 pgs.
International Search Report PCT/US2011/027566; May 11, 2011; 12 pages.
International Search Report PCT/US2011/029353; Mar. 22, 2011; 14 pages.
International Search Report PCT/US2011/029727; Feb. 3, 2012; 14 pages.
Teleangitron Operator Manual; Dated Nov. 14, 2001; 24 pages.
EMLA Description, 1 page.
European Search Report; App. No. 10157542.1-2108; Mailing Date Sep. 23, 2010; 7 pages.
International Search Report PCT/US2011/025174; Mailing Date May 4, 2011; 15 pages.
European Search Report 10157523.1-2108; Mailing Date Oct. 1, 2010; 6 pages.
European Search Report App. No. 10157528.0-2108; Mailing Date Oct. 18, 2010; 7 pgs.
"Cool Gel Cooling Hair Removal Gel"; Record ID 1519084; Church & Dwight, 3 pages; GNPD; MINTEL.
"Sensitive Hair Removal and Finishing Cream Set"; Record ID 1327122; Boots; 4 pages GNPD; MINTEL, 2010.
"Depilatory Cream"; Record ID 103645; Reckitt Benckiser; 2 pages GNPD; MINTEL, 2001.
"Soothing Hair Removal Face Cream"; Record ID 1327960; American International Industries; 5 pages GNPD; MINTEL, 2010.
European Search Report; App. No. 11180355.7-2108; Mailing Date Jan. 2, 2012; 5 pages.
European Search Report; App. No. 11180356.5-2108; Mailing Date Dec. 23, 2011; 7 pages.

(56) References Cited

OTHER PUBLICATIONS

European Search Report; App. No. 11180352.4-2108; Mailing Date Jan. 2, 2012; 8 pages.
International Search Report; PCT/US2012/051077; Mailing Date Jan. 22, 2013; 16 pages.
European Search Report; App. No. 11181559.3-2108; Mailing Date Jan. 2, 2012; 7 pages.
European Search Report; App. No. 11177832.1-2108; Mailing Date Feb. 22, 2012; 7 pages.
Marie Yvonne Caricias Hair Removal Strips, GlaxoSmithKline; published Jun. 2004, http://www.gnpd.com, 2 pages, 2004.
International Search Report, PCT/US2011/025142; Mailing Date May 11, 2011; 13 pages.
International Search Report PCT/US2011/025133; Mailing Date May 4, 2011; 16 pages.
International Search Report PCT/US2011/025145; Jun. 24, 2011; 9 pages.
International Search Report PCT/US2011/025175; Mailing Date May 4, 2011; 15 pages.
International Search Report PCT/US2011/025134; Mailing Date May 11, 2011; 14 pages.
International Search Report PCT/US2011/025148; Mailing Date Jun. 21, 2011; 10 pages.
International Search Report PCT/US2011/025147; Mailing Date Jul. 13, 2011; 10 pages.
International Search Report PCT/US2011/025176; Mailing Date Jul. 5, 2011; 12 pages.
International Search Report PCT/US2011/025135; Mailing Date Feb. 17, 2011; 11 pages.
International Search Report PCT/US2011/025150; Mailing Date Jul. 4, 2011; 12 pages.
International Search Report PCT/US2011/025177; Mailing Date Jul. 14, 2011; 14 pages.
International Search Report PCT/US2011/043611; Mailing Date Oct. 18, 2011; 11 pages.
European Search Report 10173814.4-2108; Mailing Date Feb. 10, 2011; 7 pages.
European Search Report 11165166.7-2108; Mailing Date Sep. 13, 2011; 6 pages.
European Search Report 11177837.9-2108; Mailing Date Dec. 29, 2011; 6 pages.

* cited by examiner

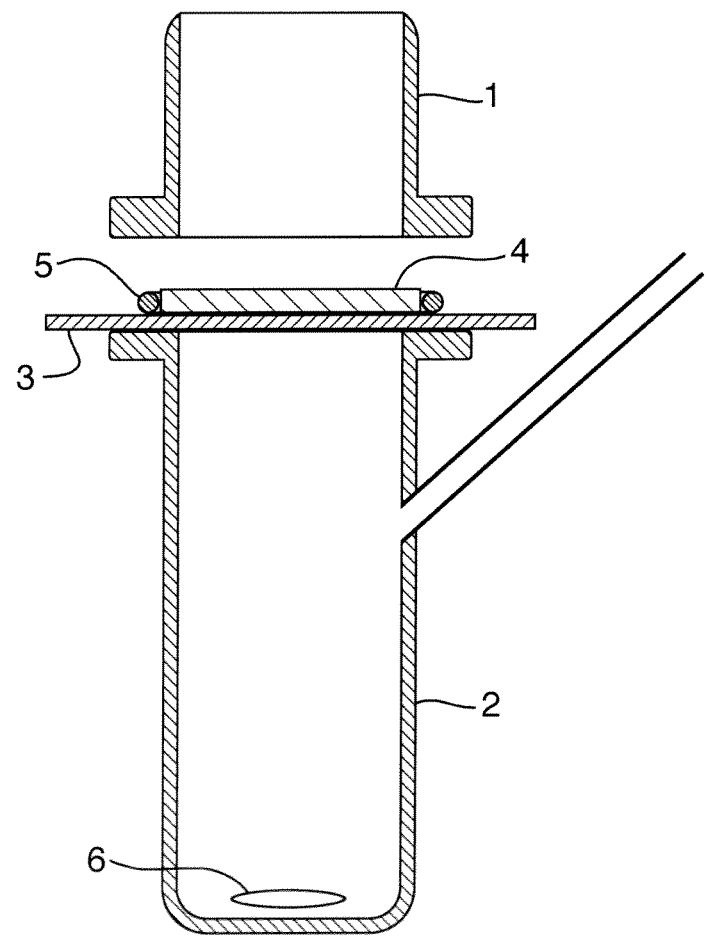

METHOD OF DEPILATION AND DEPILATORY KIT

FIELD OF THE INVENTION

The present invention relates to a depilatory method and kit.

BACKGROUND OF THE INVENTION

Depilatory compositions are cosmetic hair removal formulations. They comprise keratin reducing agents, which attack the disulphide bonds in hair to weaken it, such that subsequent gentle scraping and/or wiping completes severance of the hair from the skin and effects hair removal. Commercially, the most common keratin reducing agents are thioglycolates, which are typically formulated at high pH. An unwanted side effect of chemical depilation is that the depilatory composition comes into contact with and must have a relatively long residence time on skin to achieve effective hair removal and this long residence time combined with the alkaline conditions needed for effective hair removal may give rise to skin irritation.

The above problem has been recognized in the art. Reference is made to US 2004/0219118, which discloses treatment with a "lipophilic" material before application of a thioglycolate-based reactive depilatory compostion. Lipophilic materials exemplified in this patent application are oils, such as mineral oil. As shown hereinbelow, the present applicants have tested a range of lipophilic materials to determine their ability to prevent thioglycolate penetration and, thereby, their ability to reduce or prevent skin irritation Applicants have surprisingly found that oils, such as mineral oil, have no or a low ability to prevent thioglycolate penetration to the skin. There thus exists a need to develop a pre-treatment composition which better reduces skin irritation.

SUMMARY OF THE INVENTION

According to a first aspect of the invention a method of removing hair from skin, preferably facial skin, is provided, comprising the steps of:
(a) applying a hydrophobic protective composition to an area of skin, preferably facial skin, on which unwanted hair is growing, the hydrophobic protective composition comprising 20% or more, preferably 50% or more and more preferably from 75% to 99% of at least one triglyceride by weight of the hydrophobic protective composition, the or each triglyceride having the following formula:

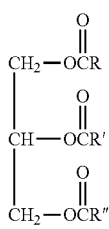

wherein R, R' and R" may be the same as or different from one or both of the others, wherein each of R, R' and R" is a fatty acid and wherein the or each triglyceride is solid at 25° C.

(b) applying a depilatory composition to the area of skin to which the hydrophobic protective composition has been applied, the depilatory composition comprising a keratin reducing agent.

According to a second aspect of the invention, a depilatory kit is provided comprising:
(a) a hydrophobic protective composition comprising 20% or more, preferably 50% or more and more preferably from 75% to 99% of at least one triglyceride by weight of the protective composition, the or each triglyceride having the following formula:

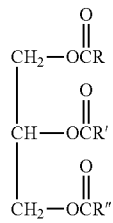

wherein R, R' and R" may be the same as or different form one or both of the others, wherein each of R, R' and R" is a fatty acid and wherein the or each triglyceride is solid at 25° C.
(b) a depilatory composition comprising an effective amount of a keratin reducing agent.

BRIEF DESCRIPTION OF THE DRAWINGS

FIG. 1. is a schematic view of a France Cell apparatus

DETAILED DESCRIPTION OF THE INVENTION

The protective composition used in the method and comprised within the kit according to the invention comprises 20% or more, preferably 50% or more and more preferably from 75% to 99% of at least one triglyceride by weight of the protective composition, the or each triglyceride having the following formula:

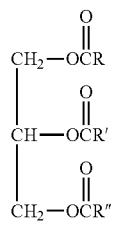

wherein R, R' and R" may be the same as or different form one or both of the others and wherein each of R, R' and R" is a fatty acid.

As demonstrated by the Franz Cell data below, the presence of the defined amounts of triglyceride in the hydrophobic protective composition surprisingly reduces penetration by thioglycolic acid in comparison with oils. Without wishing to be bound by theory, applicants believe that this may be because the wax militates against the tendency otherwise exhibited by oils to ball up on skin and therefore disrupt the barrier. The triglyceride may also ensure that a thin barrier of the hydrophobic protective composition can be evenly distributed across the skin, even at a low dosage per unit area. The triglyceride may form a barrier across the skin that is chemically resistant to ingress the thioglycolate (or other reducing) actives, therefore physically reducing the ability for the harsh chemistry to come into contact with the skin. This reduction in contact means that the stratum corneum may be maintained in a better state than if no barrier were present with correspondingly reduced signs of irritation, such as erythema, tingling and stinging. A reduction of thioglycolic acid penetration of 45% or more according to the Franz Cell method may be shown to correlate to a significant and user-noticeable reduction in irritation. Advantageously, triglyceride does not make up the entirety of the hydrophobic protective composition, because, in such a case, the composition may become difficult to handle and apply and may also be brittle, crack and fall off the skin.

At the same time as reducing contact between the depilatory active ingredient and the skin, the present compositions are observed not to noticeably reduce the ability of the depilatory composition to attack and degrade the unwanted hair growing on that skin. Why this should be is not understood, but it may simply be due to the fact that less of the hydrophobic protective composition adheres to the hairs than to the skin.

Further advantageously, the or each triglyceride has an onset temperature of less than 65° C. as measured by Differential Scanning calorimetry. At and above an onset temperature of 65° C., the composition may become increasingly difficult to apply and may even crack and fall off in use.

Suitable oils from which triglycerides may be formed from include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion in the protective composition include include Butter, Shea Butter, Butyrospermum Parkii, Theobroma Cacao (Cocoa) Seed Butter, Cocoa Butter, Hydrogenated Shea Butter, Hydrogenated Cocoa Butter, Irvingia Gabonensis Kernel Butter, Tallow, Lard, Mangifera Indica (Mango) Seed Butter, Kokum Butter and mixtures thereof.

The hydrophobic protective composition used in the method and comprised within the kit according to the invention may additionally comprise wax. If wax is additionally present, it is preferably present in an amount from 0.5% to 24%, preferably from 0.5% to 15% wax by weight of the hydrophobic protective composition. The presence of wax may provide analogous benefits to the presence of triglycerides.

As used herein, the term "wax" includes, but is not limited to, any hydrophobic material that is:
  practically insoluble in water according to the United States' Pharmacopeia (USP) definition in 31/NF 26 Vol. 2 General Notices, Page Xvii. (which, according to that definition, means that more than 10,000 parts of water are needed to dissolve 1 part solute);
  has an onset temperature measured according to the DSC Method hereinbelow starting at greater than body temperature (37° C.); and
  comprises lipids, silicones or mixtures thereof.

The wax may comprise natural wax, synthetic wax, silicone wax, or mixtures thereof.

Non-limiting examples of suitable natural waxes include Abies Alba Leaf Wax, Acacia Dealbata Leaf Wax, Acacia Farnesiana Flower Wax, Beeswax, Ceresin, Cetyl Esters, Cistus Labdaniferus Flower Wax, Aurantium Amara (Bitter Orange) Flower Wax, Aurantium Dulcis (Orange) Peel Wax, Copernicia Cerifera (Carnauba) Wax, Eclipta Prostrata Wax, Euphorbia Cerifera (Candelilla) Wax, Helichrysum Angustifolium Wax, Jasminum Officinale (Jasmine) Flower Wax, Jasminum Sambac (Jasmine) Flower Wax, Jojoba Esters, Jojoba Wax, Lanolin Wax, Lavandula Angustifolia (Lavender) Flower Wax, Lawsonia Inermis Wax, Mink Wax, Montan Acid Wax, Montan Wax, Myrica Cerifera (Bayberry) Fruit Wax, Ocimum Tenuiflorum Wax, Olive Wax, Oryza Sativa (Rice) Bran Wax, Ouricury Wax, Palm Kernel Wax, Persea Gratissima (Avocado) Wax, Pistacia Lentiscus Leaf Wax, Polianthes Tuberosa Flower Wax, Pyrus Malus (Apple) Peel Wax, Ribes Nigrum (Black Currant) Wax, Rosa Centifolia Flower Wax, Salvia Sclarea (Clary) Wax, Shellac Wax, Simmondsia Chinensis (Jojoba) Butter, Soft Olive Wax, Spent Grain Wax, Stipa Tenacissima Wax, Sunflower Seed Wax, Vegetable Wax, Vitis Vinifera (Grape) Leaf Wax and mixtures thereof.

Non-limiting examples of suitable synthetic waxes include Hydrogenated Japan Wax, Hydrogenated Jojoba Oil, Hydrogenated Jojoba Wax, Hydrogenated Microcrystalline Wax, Hydrogenated Rice Bran Wax, Hydrolyzed Beeswax, Microcrystalline Wax, Oxidized Beeswax, Oxidized Microcrystalline Wax, Ozokerite, Paraffin, PEG-6 Beeswax, PEG-8 Beeswax, PE G-12 Beeswax, PEG-20 Beeswax, PEG-12 Carnauba, Potassium Oxidized Microcrystalline Wax, Sulfurized Jojoba Oil, Synthetic Beeswax, Synthetic Candelilla Wax, Synthetic Carnauba, Synthetic Japan Wax, Synthetic Jojoba Oil, Synthetic Wax and mixtures thereof.

Non-limiting examples of suitable silicone waxes include DC2503 Cosmetic Wax, DC580 wax, DC AMS-C30 Cosmetic Wax, C30-45 Alkyl Methicone, DC Silkywax 10, Hexamethyldisiloxane, DC ST-Wax 30, C30-45 Alkyldimethylsilyl Polypropylsilsesquioxane, DC SW-8005 resin wax, C26-28 Alkyl Dimethicone, C26-28 Alkyl Methicone, Polyphenylsilsesquioxane and mixtures thereof.

Advantageously, the wax comprises beeswax, carnauba wax, candelilla wax, jojoba wax, paraffin wax, microcrystalline wax, ozokerite, arachidyl behenate, or mixtures thereof.

The hydrophobic protective composition used in the method and comprised within the kit according to the invention may comprise one or more oils. As used herein, the term "oil" includes, but is not limited to any non-aqueous substance that is practically insoluble in water according to the United States' Pharmacopeia (USP) definition in 31/NF 26 Vol. 2 General Notices, Page Xvii. (which, according to that definition, means that more than 10,000 parts of water are needed to dissolve 1 part solute) and is liquid at 20° C.

The hydrophobic protective composition used in the method and comprised within the kit according to the invention may comprise from 0.5-80% oil by weight of the hydrophobic protective composition.

The oil may be selected from natural oil, synthetic oil, silicone oil and mixtures thereof.

Non-limiting examples of suitable natural oils include Acetylated Castor Oil, Acetylated Hydrogenated Castor Oil, Actinidia Chinensis (Kiwi), Seed Oil, Adansonia Digitata Oil, Aleurites Moluccana Seed Oil, Anacardium Occidentale (Cashew) Seed Oil, Arachis Hypogaea (Peanut) Oil, Arctium Lappa Seed Oil, Argania Spinosa Kernel Oil, Argemone Mexicana Oil, Avena Sativa (Oat) Kernel Oil, Bertholletia Excelsa Seed Oil, Borago Officinalis Seed Oil, Brassica Campestris (Rapeseed) Seed Oil, Calophyllum Tacamahaca Seed Oil, Camellia Japonica Seed Oil, Camellia Kissi Seed Oil, Camellia Oleifera Seed Oil, Canola Oil, Carthamus Tinctorius (Hybrid Safflower) Seed Oil, Carthamus Tinctorius (Safflower) Seed Oil, Carum Carvi (Caraway) Seed Oil, Carya Illinoensis (Pecan) Seed Oil, Castor Oil Benzoate, Chenopodium Quinoa Seed Oil, Cibotium Barometz Oil, Citrullus Vulgaris (Watermelon) Seed Oil, Cocos Nucifera (Coconut) Oil, Cod Liver Oil, Coffea Arabica (Coffee) Seed Oil, Coix Lacryma-Jobi (Job's Tears) Seed Oil, Corylus Americana (Hazel) Seed Oil, Corylus Avellana (Hazel) Seed Oil, Cucumis Sativus (Cucumber) Oil, Cucurbita Pepo (Pumpkin) Seed Oil, Daucus Carota Sativa (Carrot) Seed Oil, Elaeis Guineensis (Palm) Kernel Oil, Elaeis Guineensis (Palm) Oil, Gossypium (Cotton) Seed Oil, Helianthus Annuus (Hybrid Sunflower) Oil, Helianthus Annuus (Sunflower) Seed Oil, Hippophae Rhamnoides Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, lsatis Tinctoria Seed Oil, Juglans Regia (Walnut) Seed Oil, Umnanthes Alba (Meadowfoam) Seed Oil, Unum Usitatissimum (Linseed) Seed Oil, Lupinus Albus Seed Oil, Macadamia Integrifolia Seed Oil, Macadamia Ternifolia Seed Oil, Maleated Soybean Oil, Mangifera Indica (Mango) Seed Oil, Marmot Oil, Melaleuca Alternifolia (Tea Tree) Leaf Oil, Melia Azadirachta Seed Oil, Melissa Officina lis (Balm Mint) Seed Oil, Menhaden Oil, Mink Oil, Moring a pterygosperma Seed Oil, Mortierella Oil, Neatsfoot Oil, Nelumbium Speciosum Flower Oil, Nigella Sativa Seed Oil, Oenothera Biennis (Evening Primrose) Oil, Olea Europaea (Olive) Fruit Oil, Olea Europaea (Olive) Husk Oil, Orange Roughy Oil, Orbignya Cohune Seed Oil, Orbignya Oleifera Seed Oil, Oryza Sativa (Rice) Bran Oil, Oryza Sativa (Rice) Germ Oil, Ostrich Oil, Oxidized Corn Oil, Oxidized Hazel Seed Oil, Papaver Orientale (Poppy) Seed Oil, Passiflora Edulis Seed Oil, Persea Gratissima (Avocado) Oil, Pistacia Vera Seed Oil, Placental Lipids, Prunus Amygdalus Amara (Bitter Almond) Kernel Oil, Prunus Amygdalus Dulcis (Sweet Almond) Oil, Prunus Armeniaca (Apricot) Kernel Oil, Prunus Avium (Sweet Chemy) Seed Oil, Prunus Cerasus (Bitter Chemy) Seed Oil, Prunus Persica (Peach) Kernel Oil, Pyrus Malus (Apple) Oil, Ribes Nigrum (Black Currant) Seed Oil, Ricinus Communis (Castor) Seed Oil, Rosa Canina Fruit Oil, Rosa Moschata Seed Oil, Salmon Oil, Salvia Hispanica Seed Oil, Santalum Album (Sandalwood) Seed Oil, Sesamum Indicum (Sesame) Seed Oil, Shark Liver Oil, Solanum Lycopersicum (Tomato) Seed Oil, Soybean Lipid, Sphingolipids, Taraktogenos Kurzii Seed Oil, Telphairia Pedata Oil, Vegetable Oil, Vitis Vinifera (Grape) Seed Oil, Zea Mays (Corn) Germ Oil, Zea Mays (Corn) Oil and mixtures thereof.

Non-limiting examples of suitable synthetic oils include mineral oil, isopropyl pamitate, isopropyl stearate, isohexadecane, isododecane, polyglyceryl triisostearate and mixtures thereof. Non-limiting examples of suitable silicone oils include dimethicones (including partial esters of dimethicones and fatty acids derived from natural/synthetic oils), cyclomethicones, polydimethlysiloxanes (such as DC200 from Dow Corning), phenyl trimethicones, trimethyl pentaphenyl trisiloxane, dimethicone copolyols and mixtures thereof.

The hydrophobic protective composition used in the method and comprised within the kit according to the invention may comprise skin active agents such as, but not limited to oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils and mixtures thereof. These materials may fall under the definition of "wax" or "oil" as used herein and, in such a case, should be included as a wax or oil for the purposes of determining the weight percentages of wax or oil.

The hydrophobic protective composition used in the method and comprised within the kit according to the invention may include further ingredients such as, but not limited to metal oxides, organic and inorganic dyes, lakes, micas, flavourings, perfumes and mixtures thereof.

Any depilatory composition comprising a suitable keratin reducing agent may be used in the present method and included in the present kit. Non-limiting examples of suitable keratin reducing agents include: sulphide salts such as $Li_2S$, $Na_2S$, $K_2S$, MgS, CaS, SrS or BaS, hydrogen sulphide salts such as NaSH or KSH; thioglycol; thioglycerol; thioglycolamide; thioglycolhydrazide; thioglycolic acid; thioglycolate salts (such as potassium thioglycolate, calcium thioglycolate, ammonium thioglycolate, diammonium dithioglycolate, glyceryl monothioglycolate, or monoethanolamine thioglycolate); thiosalicylic acid; thiomalic acid; ammonium thiolactate; monoethanolamine thiolactate; dithioerythritol; 2-mercaptopropionic acid; 1,3-dithiopropanol; glutathione; dithiothreitol; cysteine; homocysteine; N-acetyl-L-cysteine and cysteamine. Advantageously, the keratin reducing agent is comprised within the depilatory composition in an amount from 0.3% to 20%, preferably from 0.8% to 15%, more preferably from 1% to 10% by weight of the depilatory composition.

Advantageously, the depilatory composition may comprise at least one thioglycolate salt or thioglycollic acid acting as a hair removal agent when the depilatory composition is applied to unwanted hair. Preferably, the depilatory composition comprises sodium, potassium, magnesium, calcium, beryllium, strontium, zinc, monoethanolamine, ammonium, tetralkylammonium, imidazolium, pyridinium, phosphonium or glyceryl thioglycolate salts, or mixtures thereof, which may include dianion forms of thioglycolate. More preferably, the depilatory composition comprises at least one of sodium, potassium, magnesium or calcium thioglycolate, or mixtures thereof. Even more preferably the depilatory composition comprises potassium or calcium thioglycolate, or mixtures thereof.

The pH of the depilatory composition may advantageously be in the range of from 6 to 13.8, preferably from greater than 7 to 13, more preferably from 9 to 12.9, even more preferably from 10 to 12.8, even more preferably still from 12 to 12.75 and yet more preferably from 12.3 to 12.6 to improve the efficacy of the active ingredient. The depilatory composition may, in a preferred embodiment, comprise at least one base to control the pH. Preferably, the depilatory composition comprises potassium hydroxide; sodium hydroxide; lithium hydroxide; calcium hydroxide; barium hydroxide; caesium hydroxide; sodium hydroxide; ammonium hydroxide; strontium hydroxide; rubidium hydroxide; magnesium hydroxide; zinc hydroxide; sodium carbonate; pyridine; ammonia; alkanolamides (including monoethanolamine, diethanolamine, triethanolamine), phosphates (including tetrasodium phosphate), arginine or mixtures thereof. More preferably, the depilatory composition comprises at least one buffering base, even more preferably the depilatory composition comprises calcium hydroxide, magnesium hydroxide; barium hydroxide; strontium hydroxide; zinc hydroxide; arginine or mixtures thereof. Still more preferably the depilatory composition comprises calcium hydroxide; magnesium hydroxide, zinc hydroxide, sodium hydroxide, potassium hydroxide or mixtures thereof. Even more preferably still, the depilatory composition comprises calcium hydroxide, sodium hydroxide or mixtures thereof.

In an advantageous embodiment, the base is present at a concentration of from 0.1% to 10.0%, more preferably from 0.5% to 8.0% and even more preferably from 1.0% to 5.0%, by weight of the depilatory composition.

The concentration of water in the depilatory composition is preferably at least 40%, more preferably from 50% to 98%, even more preferably from 60% to 95% and even more preferably still from 70% to 90%, by weight of the depilatory composition.

The depilatory composition may optionally comprise a thickening agent. A representative but not exhaustive list can be found in "The Encyclopaedia of Polymers and Thickeners for Cosmetics" compiled and edited by Robert Y. Lochhead, PhD and William R. Fron, Department of Polymer Science, University of Southern Mississippi. Exemplary classes of thickening agents include gums, carbomers, polymers and copolymers of acrylic acid, associated thickeners, layered silicates/clays and natural polymers (including polysaccharides). One or more thickening agents may be included in the aqueous depilatory composition. The thickening agent may be present at a level of from about 0.01% to about 20%, preferably from about 0.1% to about 10% by weight of the depilatory composition.

The depilatory composition may also include other skin care ingredients such as conditioning agents selected from the group consisting of humectants, moisturizers, or skin conditioners (including mineral oil; almond oil; chamomile oil; jojoba oil; avocado oil; rhea butter, niacinamide and glycerine); skin rejuvenation compositions (for example targeted for fine lines, wrinkles and uneven skin tone, including retinoids), cosmetic compositions; anti-inflammatory agents (including corticosteroids); anti-oxidants (including flavonoids) radical scavengers; sunscreen agents; skin cooling or warming agents and the like. The depilatory composition may comprise one or more skin care ingredients present in an amount of from about 0.001% to about 10%, more preferably from about 0.01% to about 7%, and even more preferably from about 0.025% to about 5%, by weight of the depilatory composition.

An accelerant may be employed in the depilatory composition. This optional component accelerates the rate of depilatory action of the depilatory agent. Suitable accelerants include, but are not limited to, urea; thiourea; dimethyl isosorbide; arginine salts; ethoxydiglycol; propylene glycol and methylpropyldiol. The accelerant may be present in a concentration range of from 0.5% to 10%, more preferably from 2% to 8% and even more preferably from 2% to 5% by weight of the depilatory composition.

The depilatory composition may further comprise components known, conventionally used, or otherwise effective for use in cosmetic compositions, such as dyes; pigments (including ultra marines and talc); anionic, cationic, non-ionic and/or amphoteric or zwitterionic surfactants, polymers (including hydrophobically modified polymers); dispersing agents; solvents; lubricants; fragrances; preservatives; chelants, proteins and derivatives thereof, plant materials (e.g. aloe, chamomile and henna extracts); silicones (volatile or non-volatile, modified or non-modified); film-forming agents; film forming promoters and mixtures thereof.

The depilatory composition may be formulated in any common delivery form, such as a cream or lotion. Alternatively, it may be delivered on a substrate, such as a thin film of depilatory composition coated onto the substrate. The substrate may be configured in any suitable form, such as a strip, mask or patch.

In addition to the hydrophobic protective composition and the depilatory composition, the kit according to the second aspect of the invention may comprise one or more of:
  (a) A make-up removal composition and/or a make-up removal wipe;
  (b) Means for removal of the hydrophobic protective composition and the depilatory composition following use, which means may comprise one or more of a tool, such as a scraper or a spatula; or a wipe;
  (c) A post-treatment composition skin care composition to be applied to the area of skin from which hair has been removed. Such a post-treatment skin care composition may comprise ingredients to promote skin conditioning; moisturizers, skin rejuvenation compositions (targeted for fine lines, wrinkles and uneven skin tone, for example), cosmetic compositions (e.g., foundation, rouge), sunscreens and the like. The post-treatment skin care composition may be leave-on or a rinse-off composition.
  (d) Instructions regarding how to use the various elements of the kit, which instructions may comprise one or more elements of the method as defined herein.

Prior to applying the method or using the kit according to the present invention, a user should advantageously remove all make-up from the skin, to ensure good adherence and effective application of both the hydrophobic protective composition and the depilatory composition.

The method according to the first aspect of the invention comprises the step of applying the above-defined hydrophobic protective composition to an area of skin on which unwanted hair is growing. The area of skin may be located on any part of the human body, but is preferably on the face, more preferably on an area of skin adjacent to the vermillion lip and more preferably still on an area above the upper vermillion lip.

Advantageously, the hydrophobic protective composition is not just applied to the area to be depilated, but also to an immediately juxtaposing area thereabout (that is, the hydrophobic protective composition is applied to an area of skin which is greater than just the area which is to be depilated).

Advantageously, the user will apply from 0.3-2 mg of hydrophobic protective composition per square centimetre of skin, preferably from 0.4-1 mg/cm$^2$, more preferably from 0.4 to 0.7 mg/cm$^2$.

Following application, the hydrophobic protective composition is advantageously massaged into the skin: Preferably, massaging is effected for at least 10 seconds, and, more preferably, massaging is effected as a circular motion. Without wishing to be bound by theory, it is believed that the hydrophobic protective composition may trap hair within it thereby shielding it from the to-be-applied depilatory composition; massaging may help to release the hairs from the skin and ensure improved access thereto by the depilatory composition.

The method according to the first aspect of the invention comprises the subsequent step of applying the above-defined depilatory composition to an area of skin on which unwanted hair is growing and to which hydrophobic protective composition has already been applied. Advantageously, the user will apply a layer of depilatory composition which is from 0.1 mm to 5 mm, preferably from 0.3 to 3 mm, more preferably from 0.5 to 2 mm in thickness.

Subsequently, according to the method of the first aspect of the invention, the depilatory. composition is advantageously left in place for at least 1 minute, preferably from 1 to 10 minutes, more preferably from 3 to 10 minutes, depending on the thickness of the hair and the hair removal efficacy of the depilatory composition (which, in turn, is dependent upon the concentration of keratin reducing agent in the depilatory composition).

Subsequently, according to the method of the first aspect of the invention, the hydrophobic protective composition and the depilatory composition are advantageously removed. This may be achieved using one or more of a cotton wool ball, pad or wand, a tissue, a cloth, or a tool, such as a spatula or a scraper. Advantageously, the skin from which hair has been removed is then rinsed with water.

In an advantageous subsequent step, a post-treatment skin care composition may be applied to the area of skin from which hair has been removed. Such a post-treatment skin care composition may comprise ingredients to promote skin conditioning; moisturizers, skin rejuvenation compositions (targeted for fine lines, wrinkles and uneven skin tone, for example), cosmetic compositions (e.g., foundation, rouge), sunscreens and the like. The post-treatment skin care composition may be leave-on or a rinse-off composition.

Differential Scanning calorimetry (DSC) Melting Method

This method is the American Oil Chemists' Society Method Cj 1-94, as reapproved in 2009 and it determines the "onset temperature" (that is the temperature of onset of melting) of oils and fats by differential scanning calorimetry (DSC).
Apparatus
 1. Aluminum capsules.
 2. DSC instrument, capable of holding temperature at −60° C. and achieving a temperature of 80° C.
Reagents
 1. Indium, powder—60 mesh, 99.999%, such as Aldrich Chemical Co., Milwaukee, Wis. 53233, or equivalent.
 2. n-Decane, 99+%, such as Aldrich Chemical Co., Milwaukee, Wis. 53233, or equivalent.
 3. Methyl stearate, 99%, such as Aldrich Chemical Co., Milwaukee, Wis. 53233, or equivalent.
Procedure
 1. Standardization of equipment—Proceed with the normal standardization using both indium and n-decane as reference standards. Follow instrument manual for adjustment to lock onto these two reference points and flatten the baseline slope as much as possible when empty pans are analyzed. Analyze the secondary standard (methyl stearate). Weigh 5 mg of the standard into the same kind of pan which will be used for the test portion (if hermetically sealed, it may be reused at a later date). Use the method sequence in Procedure, 2-7 to obtain the melting point onset (because of the high purity, only a 2 min hold is necessary for the standard after crystallization). Be certain that the heating rate during the definitive heating pattern is at 5° C./min. The melting point onset should be within ±2.00° C. of 36.5° C. If not, recheck calibration.
 Note—be certain to use identical capsules for the test portion as those used for reference standards and the instrument blank reference.
 2. Melt each test portion completely and weigh 7±0.200 mg of each test portion into the same kind of capsule used for the blank and reference samples (aluminum) and seal to minimize oxidation and other changes.
 3. Place capsules in DSC at room temperature.
 4. Heat rapidly to 80° C. and hold for 10 min.
 5. Cool to −60° C. at 10° C./min and hold for 30 min.
 6. Heat to 80° C. at 5° C./min.
 7. Use the baseline obtained for an empty capsule analysis from the final melt segment of the program to define the position of the baseline under the sample peaks. Overlay the final melting curve of the test portion over the curve for the empty capsule with a flexible ruler or other curve guide to define the baseline of the test portion back to where it intersects the initial deviation of the melting curve from its baseline. The baseline beneath the test portion should be a continuation of the baseline where there are no sample components present. If a shift has occurred in the heat capacity of the test portion after the melt, it will be evident relative to the baseline of the empty capsule. Have the instrument calculate the sigmoid baseline if it can, or connect the end of the peak point with the last point in which the test portion was in conjunction with the baseline of the empty capsule.
Results
 Determine the onset temperature in ° C., which, if not computer generated, is an extrapolation to baseline of the steepest slope of the principal peak.

Franz Cell Method

Principle and Scope:
 This method is applicable for using Franz cell apparatus for the in-vitro assessment of penetration of thioglycolic acid (TGA) and its salts through a skin mimic after the application of a depilatory composition following pre-treatment with a hydrophobic protective composition.
 Penetrated TGA is quantified using Reverse Phase High Performance (or Pressure) Liquid Chromatography (RP-HPLC) with external standard quantitation at 240 nm.
Method
 Reference is made to FIG. 1 and to the reference numerals therein:
 1. Prepare the vitro-skin (IMS Vitro-Skin®, Catalogue number: P&G1013, made by IMS Inc., Portland, Me., USA) samples by cutting 8×6.2 cm segments and placing them textured side up on the racks into a hydration chamber (manufactured & sold by IMS) containing a 14.7% glycerol solution. The hydration chamber should be sealed and the vitro-skin left to hydrate at room temperature and a humidity of 80.4%±3.5% for 24 hours.
 2. Prepare the receptor solution for the Franz-cell by mixing 1.90 ml formic acid (98% wt+Fluka, by Sigma Aldrich, or equivalent), 30 ml acetonitrile (RP-HPLC grade) and 968.1 ml water (RP-HPLC grade). Set up the static Franz cell (Permegear or equivalent, 15 mm diameter unjacketed cell with a 12 ml receptor volume) by clamping it in place over suitable stirrer plates (not shown) and add a small stirrer bar (6) to each cell, fill the receptor cell (2) to the brim with the required amount of receptor solution.
 3. Once hydrated, remove a sheet of vitro-skin from the hydration chamber and lay textured side up on a clean flat surface then dose 100 µl (~2 mg/cm$^2$) of hydrophobic protective composition (not shown) onto the vitro-skin and spread evenly over the surface by rubbing for 30 seconds with a gloved finger.
 4. Using a scalpel blade cut the vitro-skin segment (3) into two equal sections, each large enough to completely cover the top of the cell. Place the relevant size o-ring (5) (22 mm, for the specified Franz-cell) onto each section of the vitro skin and dose to 150 mg/cm$^2$ of depilatory composition (4) ("Veet Normal Skin Hair Removal Cream" or an equivalent (an equivalent being a composition comprising 3.7% wt thioglycolic acid)) into the centre then, using a glass rod, evenly spread the cream around the inside of the o-ring (5). Using tweezers pick up the vitro-skin segment and place the vitro-skin segment, depilatory and o-ring centrally over the receptor cell (2), place donor cell (1) over the top and clamp in place. Turn on stirrer plate and start 10 minute countdown timer. After 10 minutes; turn off stirrer and remove the clamp, donor cell (1) and vitro-skin segment and place the receptor solution in a suitable container for analysis.

5. A reference sample should also be run without hydrophobic protective composition treatment on the vitro-skin. Remove a sheet of vitro-skin from the hydration chamber and lay textured side up on a clean flat surface. Repeat step 4 of the protocol to produce the reference sample.

Sample Analysis

For RP-HPLC analysis, prepare a 50 mM Formic acid (98%+Fluka) solution and mix 970 ml of this solution with 30 ml acetonitrile (HPLC grade) to act as a mobile phase during the analysis.

A reference standard solution should be made with a concentration of Calcium Thioglycolate Trihydrate of 0.94 mg/ml.

Install a Waters Atlantis T3 3 μm 4.6×50 mm column into the HPLC (although any silica-based $C_{18}$ reversed phase RP-HPLC column may be used), and ensure all solvent lines for the RP-HPLC are primed and free of leaks. Allow the mobile phase to circulate through the system for 25 minutes at 0.7 mL/Min in order to equilibrate the column. Detection of the thioglycolic acid is via UV spectroscopy.

The RP-HPLC conditions are as follows:
Injection volume: 20 μL
Mobile phase flow rate: 0.70 ml/min
Run time: 10 minutes
UV Detection wavelength: 240 nm
Column temperature: 35° C.
UV sampling rate: ≥5 per second
Retention time: Thioglycolic Acid ~2.5 min Calculations:

Calculate the concentration of Thioglycolic Acid in the sample $$\text{concentration(mg/ml)} = \frac{\text{weight of } std\text{(mg)} \times \text{purity}}{25} \times \frac{3}{25}$$

Calculate the concentration of thioglycolic acid in the sample using the following formula:

$$\text{concentration (mg/ml)} = A/B \times C \times E/F$$

Where,
A=Peak Area of Thioglycolic Acid Sample
B=Average Peak Area of Thioglycolic Acid Standard
C=Thioglycolic Acid final STD concentration in mg/ml (0.94 mg/ml)
E=Molecular weight of Thioglycolic acid (92.12 g/mol)
F=Molecular weight of Calcium thioglycolate (184.23 g/mol)

The efficacy of the barrier (resistance to TGA penetration) can be calculated as a percentage decrease in TGA in the receptor solution:

$$\% \text{ reduction} = \frac{\text{concentration without barrier} - \text{concentration with barrier}}{\text{concentration without barrier}} \times 100$$

For example, if TGA in solution without hydrophobic protective composition=75 μg/ml and TGA in solution with barrier=15 μg/ml $$\% \text{ reduction} = \frac{75 - 60}{75} \times 100 = 85\%$$

A reduction of TGA penetration of 45% or more is believed to correlate to a significant and user-noticeable reduction in irritation.

EXAMPLES

The following compositions were made by heating all elements of the composition to the melting temperature of the wax and then mixing until a homogenous mixture was obtained. The compositions were then tested using the Franz Cell method defined above.

| Example | Composition | % Reduction in Thioglycolic Acid Penetration (According to the Franz Cell Method) |
|---|---|---|
| Inventive Example 1 | 2% mineral oil 98% shea butter | 86.3 |
| Inventive Example 2 | 25% olive oil 75% cocoa butter | 95.1 |
| Comparative Example 1 | 100% mineral oil | 25.0 |
| Comparative Example 2 | 12% cocoa butter 88% mineral oil | 21.1 |
| Comparative Example 3 | 12% shea butter 88% mineral oil | 20.1 |
| Comparative Example 5 | 100% sunflower seed oil | 10.8 |
| Comparative Example 4 | 100% olive oil | 0.0 |

As demonstrated by the Franz Cell data, oils, on their own (see Comparative Examples 1 and 4), or mixed with small amounts of triglycerides (see Comparative Examples 2 and 3), such as those comprised within shea or cocoa butter, provide little to no barrier to thioglycolic acid, whereas the addition of a small amount of wax surprisingly increases the barrier to penetration by a significant amount (see Inventive Example 1).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of removing, hair from skin, comprising the steps of:
    (a) applying a hydrophobic protective composition to an area of skin on which unwanted hair is growing, the hydrophobic protective composition comprising a homogenous mixture of:
       1) about 75 to 98% of at least one triglyceride by weight of the hydrophobic protective composition, each triglyceride having the following formula:

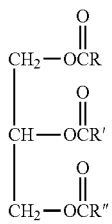

wherein R, R' and R" may be the same as or different from one or both of the others, wherein each of R, R' and R" is a fatty acid and each triglyceride is solid at 25° C., wherein the hydrophobic protective composition reduces the percent of thioglycolic acid penetration by at least 45% according to the Franz Cell Method, and wherein said at least one triglyceride is selected from shea butter, cocoa butter, and a mixture thereof;
       2) 2 to about 25% of an oil, wherein the oil is selected from olive oil, mineral oil, and a mixture thereof; and
    (b) applying a depilatory composition to the area of skin to which the hydrophobic protective composition has been applied, the depilatory composition comprising a keratin reducing agent.

2. The method of claim 1, wherein the amount of hydrophobic protective composition applied to the skin is from about 0.3 - about 2 mg/cm².

3. The method of claim 1, wherein the depilatory composition is applied as a layer to the skin which has been pretreated with the hydrophobic protective composition, wherein the layer has a thickness from about 0.1 mm to about 5 mm.

4. The method of claim 1, comprising the following additional step between step (a) and step (b):
    (a1) massaging the hydrophobic protective composition into the skin for at least 10 seconds.

5. The method of claim 1, comprising the following additional step immediately following step (b):
    (c) leaving the depilatory composition in place on the hydrophobic protective composition for a period of at least about 1 minute.

6. The method of claim 1, comprising the following additional step immediately following step (b):
    (c) leaving the depilatory composition in place on the hydrophobic protective composition for a period of about 3 to about 10 minutes.

7. The method of claim 6, comprising the following additional step immediately following step (c):
    (d) removing both the hydrophobic protective composition and the depilatory composition from the skin by a method selected from the group consisting of scraping, wiping or rubbing it off.

8. The method according to claim 1, wherein each triglyceride has an onset temperature of less than about 65° C. as measured by Differential Scanning Calorimetry.

9. The method of claim 1, wherein the keratin reducing agent is selected from the group consisting of potassium thioglycolate, calcium thioglycolate and mixtures thereof.

10. A method of removing hair from skin, comprising the steps of:
    (a) applying the hydrophobic protective composition of claim 1 to an area of skin on which unwanted hair is growing;
    (a1) massaging the hydrophobic protective composition into the skin for at least about 10 seconds;
    (b) applying a depilatory composition to the area of skin to which the hydrophobic protective composition has been applied, the depilatory composition comprising a keratin reducing agent;
    (c) leaving the depilatory composition in place on the hydrophobic protective composition for a period of about 3 to about 10 minutes; and
    (d) removing both the hydrophobic protective composition and the depilatory composition from the skin.

* * * * *